(12) United States Patent
Tegenthoff et al.

(10) Patent No.: US 8,046,083 B2
(45) Date of Patent: Oct. 25, 2011

(54) DEVICE FOR INFLUENCING BRAIN FUNCTIONS OF A HUMAN BEING

(76) Inventors: Martin Tegenthoff, Unna (DE); Hubert Dinse, Fröndenberg (DE)

( * ) Notice: Subject to any disclaimer, the term of this patent is extended or adjusted under 35 U.S.C. 154(b) by 265 days.

(21) Appl. No.: 11/851,079

(22) Filed: Sep. 6, 2007

(65) Prior Publication Data

US 2008/0065174 A1 Mar. 13, 2008

(30) Foreign Application Priority Data

Sep. 6, 2006 (DE) .......................... 10 2006 042 156

(51) Int. Cl.
*A61N 1/04* (2006.01)
(52) U.S. Cl. .................. 607/72; 607/1; 607/2; 607/115; 607/142; 607/149; 607/150
(58) Field of Classification Search .................. 607/1–2, 607/72, 115, 142, 144–145, 149, 150
See application file for complete search history.

(56) References Cited

U.S. PATENT DOCUMENTS

| 1,514,746 | A  | * | 11/1924 | Wappler .......................... 607/72 |
| 6,615,080 | B1 | * | 9/2003  | Unsworth et al. ................. 607/2 |
| 2004/0073271 | A1 |   | 4/2004  | Harry et al. |
| 2004/0167588 | A1 | * | 8/2004  | Bertolucci ...................... 607/72 |
| 2005/0203586 | A1 | * | 9/2005  | Yu ................................... 607/46 |
| 2006/0030897 | A1 |   | 2/2006  | Gilmer et al. |

FOREIGN PATENT DOCUMENTS

DE 41 39 535 A1 6/1993
DE 102 17 954 A1 7/2003

* cited by examiner

*Primary Examiner* — Carl H Layno
*Assistant Examiner* — Deborah Malamud
(74) *Attorney, Agent, or Firm* — Laurence A. Greenberg; Werner H. Stemer; Ralph E. Locher

(57) ABSTRACT

Device for influencing brain functions of a human being by targeted stimulation of at least one region of the human body, comprising stimulating means that permit a stimulation of the region that is to be stimulated, characterized in that the stimulation is an electrical stimulation.

24 Claims, 2 Drawing Sheets

DEVICE FOR INFLUENCING BRAIN FUNCTIONS OF A HUMAN BEING

BACKGROUND OF THE INVENTION

Field of the Invention

The present invention relates to a device for influencing brain functions of a human being, in accordance with the preamble of claim 1.

In persons suffering from medical conditions, or in elderly persons, it is desirable to eliminate or to alleviate sensory or sensorimotor deficits. Examples of these are the treatment of age-related deterioration of the sensitivity of the hands caused by various physiological and pathological processes during aging. Other examples are the treatment of patients suffering from involuntary movements (dystonia), particularly in the area of the upper and lower limbs, of patients who have been immobilized for a long period of time, and of patients with cerebral paralyses, in order to improve the sensorimotor function of the limbs following a stroke. It is also desirable to improve tactile awareness in persons who are blind or severely visually impaired. A further fundamental problem, especially in the elderly and in persons who have sustained injury to the central and/or peripheral nervous system, is an increased tendency to suffer falls, because of an impaired gait function. This impairment is in many cases due to reduced sensitivity in the feet and legs.

A device of the type mentioned at the outset is known from DE 10 2004 039 350 A1. With said device, a human being's finger tip, for example, is mechanically stimulated by two small points that are moved toward and away from the surface of the skin with a defined frequency. Such a device is comparatively complicated to construct and, in terms of the stimulation that can be achieved, requires some improvement.

BRIEF SUMMARY OF THE INVENTION

The problem addressed by the present invention is to make available a device, of the type mentioned at the outset, which has a simpler and/or more effective structure.

According to the invention, this is achieved by a device with the features of claim 1. The dependent claims concern preferred developments of the invention.

The device according to the invention is intended to influence brain activity in humans by means of targeted electrical stimulation of selected regions of the skin, in order in this way to improve perception and response.

The principle of such changes is based on the fact that the brain posesses a high degree of plasticity. The triggering of plasticity itself is subject to precise, defined boundary conditions. These are deliberately exploited by the invention. As a result, mechanisms at a cellular and subcellular level are set in motion that lead to changes in the synaptic transmission capacity in the brain. These in turn alter the way in which the neuronal networks of the brain process information from the environment.

A device according to the invention can be designed in accordance with the following description in which reference is made to the attached drawing, in which:

DESCRIPTION OF THE INVENTION

Figure 1:
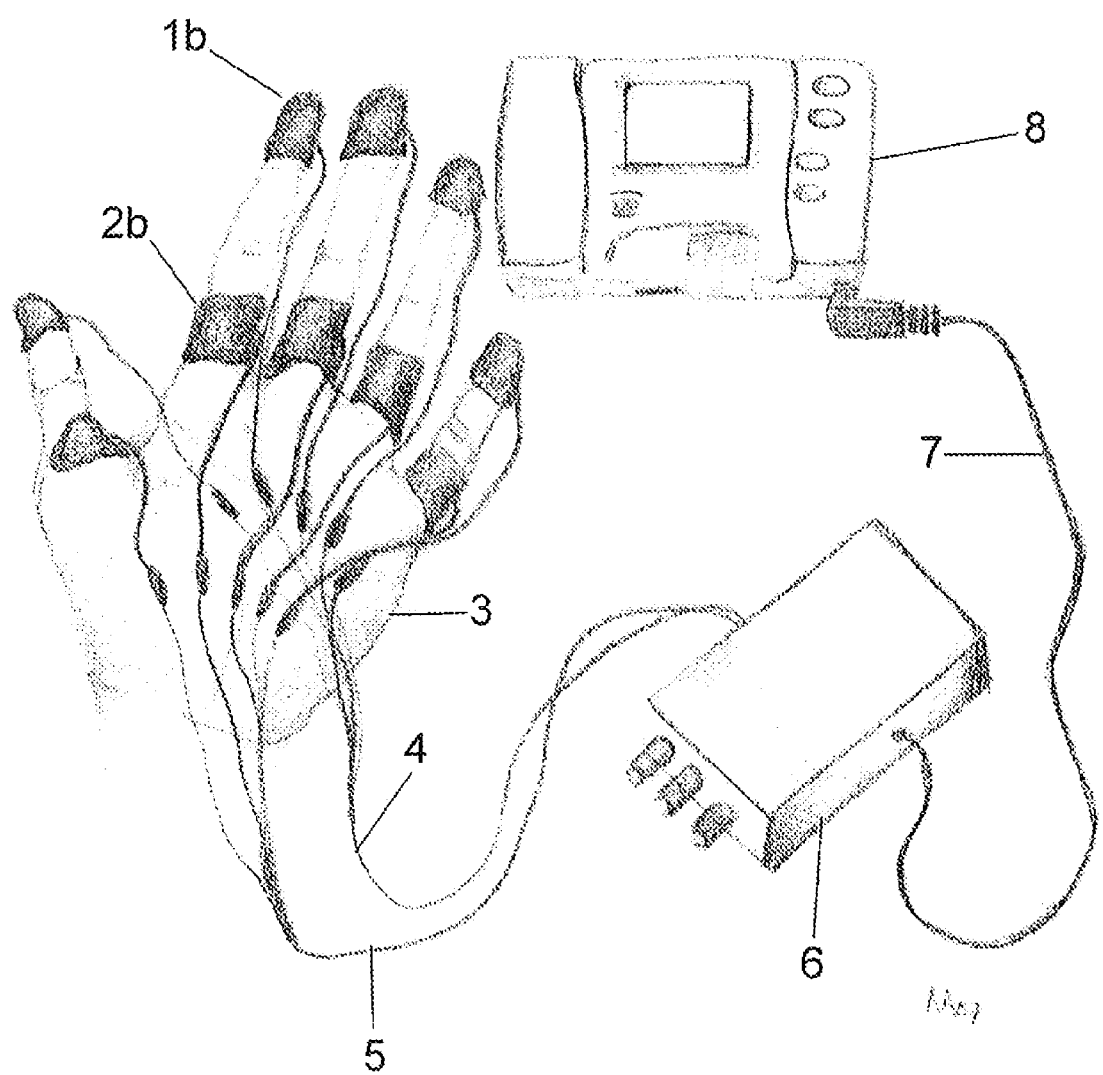
FIG. 1 shows a schematic depiction of a device according to the invention, with electrodes placed on the fingers of a human being.

The embodiment of a device according to the invention depicted in FIG. 1 comprises a plurality of electrodes 1a, 1b, 1c, 1d, 1e; 2a, 2b, 2c, 2d, 2e, of which in each case two are placed on each finger of a human hand 3. One of the electrodes 1a, 1b, 1c, 1d, 1e is in each case placed on the distal phalanx of the fingers of the hand 3, and another of the electrodes 2a, 2b, 2c, 2d, 2e is in each case placed on the proximal phalanx of the fingers of the hand 3 (see also FIG. 2).

Electrical supply lines 4a, 4b, 4c, 4d, 4e to all the electrodes 1a, 1b, 1c, 1d, 1e arranged on the distal phalanges are combined to form a first common supply line 4. Moreover, supply lines 5a, 5b, 5c, 5d, 5e to all the electrodes 2a, 2b, 2c, 2d, 2e arranged on the proximal phalanges are combined to form a second common supply line 5. The common supply lines 4, 5 are connected to a control unit 6 which, for example, is principally composed of a current generator. The control unit 6 is connected to a data memory unit 8 via a cable 7.

Figure 2:
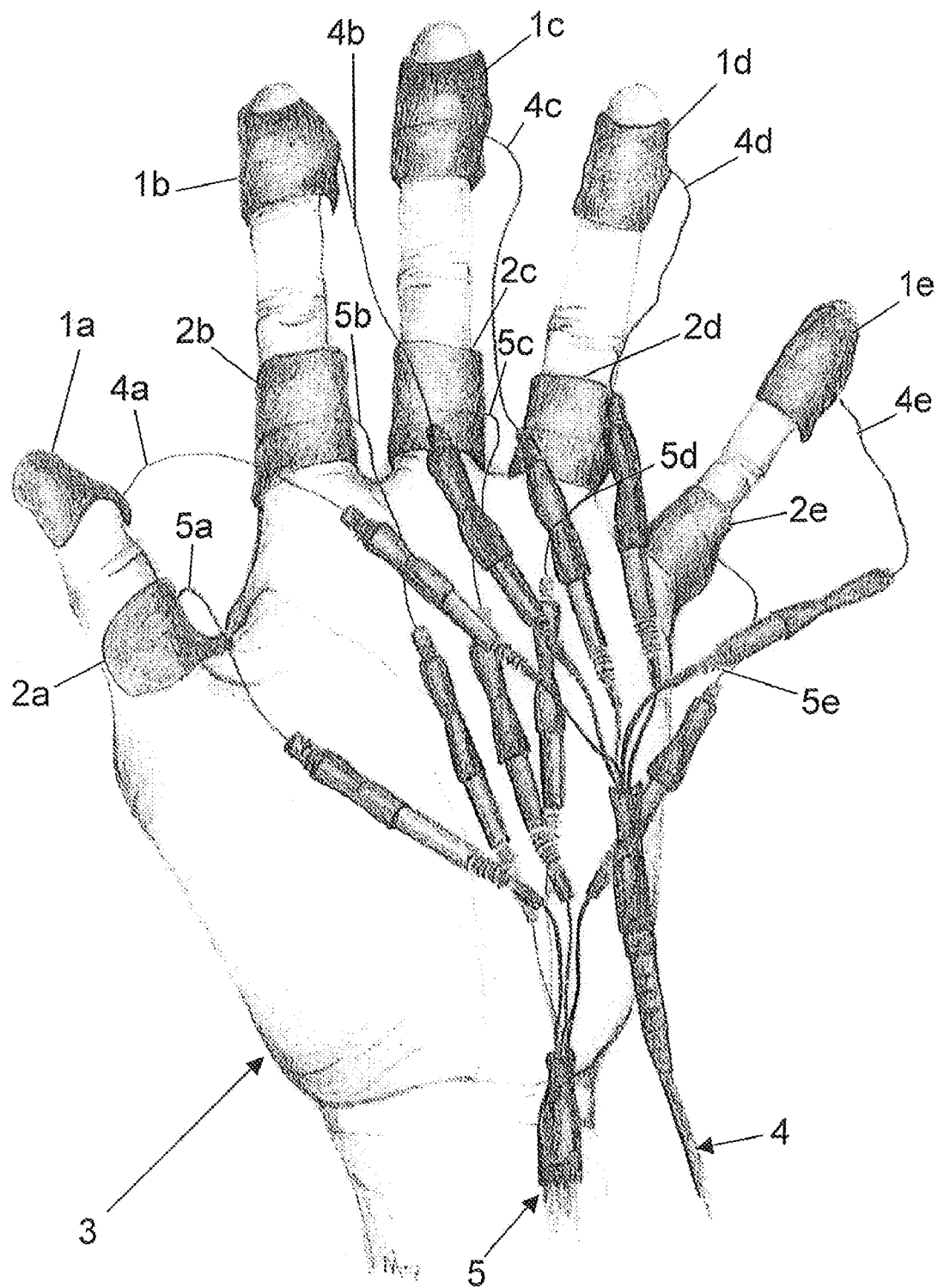
FIG. 2 shows an enlarged representation of a human hand, with the electrodes according to FIG. 1.

The electrodes 1a, 1b, 1c, 1d, 1e; 2a, 2b, 2c, 2d, 2e are, for example, commercially available self-adhesive surface electrodes which are affixed to defined regions of the skin, for example the areas of the fingers shown in FIG. 2. Electrical pulses are transmitted to these defined regions of the skin. A current whose strength corresponds to the stimulation intensity flows through the patient's skin between two electrodes 1a, 1b, 1c, 1d, 1e; 2a, 2b, 2c, 2d, 2e placed on a finger. The stimulation of the electrodes 1a, 1b, 1c, 1d, 1e; 2a, 2b, 2c, 2d, 2e is effected with the aid of electrical pulse sequences. These are emitted from the data memory 8, for example a portable data carrier that can be designed as a walkman, CD player or MP3 player, and supplied to the electrodes 1a, 1b, 1c, 1d, 1e; 2a, 2b, 2c, 2d, 2e via a likewise portable and correspondingly small electrical amplifier, which is integrated in the control unit 6 or forms the latter. The possibility exists of integrating the data memory 8 and the control unit 6 into one appliance, which in particular can be made portable and light.

To make it easier to apply the electrodes 1a, 1b, 1c, 1d, 1e; 2a, 2b, 2c, 2d, 2e to the fingers or finger tips, they can be arranged on a foil in such a way that they can be easily affixed to the finger pads of the fingers of one hand.

The manner of influencing the brain activity is determined by the time structure of the pulse sequences (frequency, pulse duration, number of stimuli, pauses between stimuli, total duration of the stimulation).

For example, the current strength can be adapted to the individual sensitivity threshold and is generally between 5 mA and 7 mA. The stimulation can be in the form of individual pulses with a duration of in each case 10 milliseconds. Different protocols can be employed for the stimulation sequence. One possible protocol entails a pulse sequence of 20 Hz lasting for 1 second, followed by a pause of 5 seconds. Such a sequence can be repeated a total of 20 to 30 minutes.

An application for 20 to 30 minutes is sufficient to trigger detectable changes in the brain. To stabilize the changes triggered in this way in the brain, the stimulations can be repeated at intervals of a few days.

The advantage of the method lies in the short application time and in the fact that the stimulation can take place passively, without active input on the part of the user and without the latter monitoring the stimulation. It is even possible to go for a walk or do some reading during the stimulation. These advantages are particularly important for persons whose active cooperation is limited.

To achieve an improvement in the sensory functions important for standing and walking, and in the sensorimotor deficits induced by disease in patients with an impaired gait function, a stimulation system can be used which, in contrast to the finger stimulation described above, stimulates the soles of the feet using the method described above.

The device according to the invention can solve the following problems:

1. Maintaining Everyday Competence in Elderly Persons by Means of Passive Sensory Stimulation
   a. In the Context of Gait Functions A central problem for the elderly lies in their increased tendency to suffer falls as a result of a deterioration in gait function. This deterioration is in many cases due to reduced sensitivity in the feet and legs. To achieve an improvement in this sensory function important for standing and walking, the device according to the invention can systematically stimulate the soles of the feet under defined timing conditions.

b. In the Context of Finger/Hand Functions

Another problem making it difficult to maintain the ability to undertake everyday tasks (everyday competence) is the age-related impairment of finger sensitivity. To achieve an improvement in this sensory function important for tasks involving the fingers and hands, the device according to the invention can systematically stimulate the finger tips under defined timing conditions. This stimulation is performed daily for short periods of time.

2. Passive Sensory Stimulation for Patients Following Brain Damage

In accordance with the principle described under 1, the device according to the invention can be used to systematically stimulate selected body regions under defined timing conditions. The patients in question are those who have suffered contralateral brain damage (e.g. stroke, cerebral hemorrhage, traumatic brain damage), in order to treat sensorimotor deficits. The stimulations are performed in a similar way.

3. Treatment of Pain by Means of Passive Sensory Stimulation

Patients with chronic pain syndromes of a specific type, in particular in the area of the upper and lower limbs. Systems such as those described under 1 are used.

4. Treatment of Sensory Deficits Caused by Prolonged Immobilization (Plaster Cast), by Means of Passive Sensory Stimulation Sensorimotor deficits arise as a result of prolonged periods of immobilization of the upper and lower limbs. These deficits are to be counteracted by application of sensory stimulation. This is done by incorporating the stimulating means into the plaster cast.

5. Passive Sensory Stimulation for Patients Suffering from Dystonia

In accordance with the principle described under 1, the device according to the invention can be used to systematically stimulate the affected fingers or the affected hand under defined timing conditions. The patients in question are those suffering from localized motor disturbance in the form of a dystonia in the area of a limb. The stimulations are performed in a similar way.

The invention claimed is:

1. A device for influencing brain functions of a human body by targeted stimulation of at least one region of the body, comprising:
   a stimulating unit for stimulating the region of the body that is being stimulated, said stimulating unit being constructed to produce an electrical stimulation that improves a sensory function selected from the group consisting of a first sensory function related to standing and walking and a second sensory function related to tasks involving fingers and hands;
   said stimulating unit emitting a sequence of electrical pulses;
   said stimulating unit producing a pause after a sequence of electrical pulses and after the pause emitting a further sequence of electrical pulses; and
   the pause between sequences of pulses being greater than a duration of the sequences of pulses;
   wherein said stimulating unit includes at least two electrodes for removable contact with a surface of the region of the body that is being stimulated, and said at least two electrodes are spaced apart from each other a distance of between 15 mm and 150 mm.

2. The device of claim 1, wherein said stimulating unit is constructed to be brought at least partially into contact with the region of the body that is being stimulated.

3. The device of claim 1, wherein said stimulating unit emits pulses having a duration of between 1 ms and 100 ms.

4. The device of claim 1, wherein said stimulating unit emits pulses having a duration of between 3 ms and 50 ms.

5. The device of claim 1, wherein said stimulating unit emits pulses having a duration of between 5 ms and 20 ms.

6. The device of claim 1, wherein said stimulating unit emits pulses having a duration of 10 ms.

7. The device of claim 1, wherein the sequences of pulses each is less than half as long as the pause.

8. The device of claim 1, wherein said at least two electrodes are spaced apart from each other a distance of between 30 mm and 50 mm.

9. The device of claim 1, wherein said at least two electrodes are spaced apart from each other a distance of 20 mm.

10. The device of claim 1, wherein:
    said at least two electrodes are finger electrodes configured for placement on one or more fingers of the human body.

11. The device of claim 1, wherein said at least two electrodes are configured for placement on at least one sole of a foot of the human body.

12. The device of claim 1, wherein said device includes a data memory to store information corresponding to the electrical pulses.

13. The device of claim 12, wherein said data memory is constructed as a portable data carrier.

14. The device of claim 1, wherein said stimulating unit causes a surface of the at least one region of the body to be stimulated systematically in accordance with defined timing conditions.

15. The device of claim 1, wherein the electrical stimulation has a strength of 0.5 mA to 20 mA.

16. The device of claim 1, wherein the electrical stimulation has a strength of 3 mA to 10 mA.

17. The device of claim 1, wherein the electrical stimulation has a strength of 5 mA to 7 mA.

18. The device of claim 1, wherein said device comprises a control unit to supply current to said electrodes.

19. The device of claim 1, wherein said device is portable.

20. The device of claim 1, wherein said device has a weight of less than 3 kg.

21. The device of claim 1, wherein said device has a weight of less than 0.5 kg.

22. The device of claim 1, wherein said at least two electrodes are finger electrodes configured for placement on one or more fingers of the human body; and the electrical stimulation produced by said stimulating unit improves the second sensory function related to tasks involving fingers and hands.

23. The device of claim 1, wherein said at least two electrodes are configured for stimulating one or more feet of the human body; and the electrical stimulation produced by said stimulating unit improves the first sensory function related to standing and walking.

24. A device for influencing brain functions of a human body by targeted stimulation of at least one region of the body, comprising:
- a stimulating unit for stimulating the region of the body that is being stimulated, said stimulating unit being constructed to produce an electrical stimulation that improves a sensory function selected from the group consisting of a first sensory function related to standing and walking and a second sensory function related to tasks involving fingers and hands;
- said stimulating unit emitting a sequence of electrical pulses;
- said stimulating unit producing a pause after a sequence of electrical pulses and after the pause emitting a further sequence of electrical pulses; and
- the pause between sequences of pulses being greater than a duration of the sequences of pulses;
- wherein said device has a weight of less than 5 kg.

* * * * *